(12) United States Patent
Lim et al.

(10) Patent No.: US 12,167,897 B2
(45) Date of Patent: Dec. 17, 2024

(54) ROBOT ARM STRUCTURE AND SURGICAL ROBOT MANIPULATOR INCLUDING SAME

(71) Applicant: MEERE COMPANY INC., Hwaseong-si (KR)

(72) Inventors: Yo An Lim, Hwaseong-si (KR); Kil Hwan Choi, Seongnam-si (KR); Jin Ah Sim, Gwangju-si (KR); Chang Gil Jung, Seoul (KR); Dong Soo Kim, Hwaseong-si (KR)

(73) Assignee: MEERE COMPANY INC., Hwaseong-si (KR)

( * ) Notice: Subject to any disclaimer, the term of this patent is extended or adjusted under 35 U.S.C. 154(b) by 1038 days.

(21) Appl. No.: 17/251,611

(22) PCT Filed: Jun. 11, 2019

(86) PCT No.: PCT/KR2019/006975
§ 371 (c)(1),
(2) Date: Dec. 11, 2020

(87) PCT Pub. No.: WO2019/240453
PCT Pub. Date: Dec. 19, 2019

(65) Prior Publication Data
US 2021/0244489 A1    Aug. 12, 2021

(30) Foreign Application Priority Data

Jun. 12, 2018   (KR) .................. 10-2018-0067532
Jan. 24, 2019   (KR) .................. 10-2019-0009232

(51) Int. Cl.
*A61B 34/30*      (2016.01)
*A61B 90/50*      (2016.01)
(Continued)

(52) U.S. Cl.
CPC .............. *A61B 34/30* (2016.02); *A61B 90/50* (2016.02); *B25J 18/00* (2013.01); *A61B 34/37* (2016.02)

(58) Field of Classification Search
CPC ......... A61B 34/30; A61B 90/50; A61B 34/37; B25J 18/00
See application file for complete search history.

(56) References Cited

U.S. PATENT DOCUMENTS 10,758,313 B2 *   9/2020   Bernstein .............. A61B 90/11
11,166,770 B2 *   11/2021  DiMaio ................. A61B 34/00
(Continued)

FOREIGN PATENT DOCUMENTS

WO    WO 2017/062370 A1    4/2017
WO    WO 2018/052795 A1    3/2018

OTHER PUBLICATIONS

International Search Report and Written opinion dated Sep. 17, 2019 in international Application No. PCT/KR2019/006975, in 13 pages. (English translation of ISR.).

*Primary Examiner* — Shirley X Jian
(74) *Attorney, Agent, or Firm* — Knobbe, Martens, Olson & Bear, LLP

(57) ABSTRACT

This application relates to a robot arm structure and a manipulator of a surgical robot including the robot arm structure. The robot arm structure includes a first robot arm unit and a second robot arm unit. The first robot arm unit includes a plurality of first link arms, a first joint unit mounted on one of the first link arms and rotating the one of the first link arms about a first axis and a second joint unit installed on at least one of the plurality of first link arms to adjust a length of the at least one link arm. The second robot arm unit includes a second link arm connected to one of the first link arms and a third joint unit using a lengthwise (Continued)

direction of the second link arm as a first rotary shaft and rotating the second link arm.

18 Claims, 7 Drawing Sheets

(51) Int. Cl.
    *B25J 18/00*     (2006.01)
    *A61B 34/37*     (2016.01)

(56)     References Cited

U.S. PATENT DOCUMENTS

| | | | |
|---|---|---|---|
| 11,564,760 B2 * | 1/2023 | Steger | A61B 90/50 |
| 11,690,691 B2 * | 7/2023 | Yakimovich | B25J 18/04 |
| | | | 606/1 |
| 11,717,361 B2 * | 8/2023 | Rockrohr | A61B 18/14 |
| | | | 606/130 |
| 2005/0096502 A1 | 5/2005 | Khalili | |
| 2013/0239392 A1 | 9/2013 | Solomon et al. | |
| 2017/0181801 A1 | 6/2017 | Griffiths et al. | |
| 2019/0216555 A1 * | 7/2019 | DiMaio | B25J 9/1664 |
| 2021/0401517 A1 * | 12/2021 | Abbott | A61B 34/35 |
| 2022/0022980 A1 * | 1/2022 | DiMaio | A61B 50/13 |

* cited by examiner

ROBOT ARM STRUCTURE AND SURGICAL ROBOT MANIPULATOR INCLUDING SAME

CROSS-REFERENCE TO RELATED APPLICATIONS

This application is a national phase of PCT Application No. PCT/KR2019/006975, filed on Jun. 11, 2019, which claims priority to Korean Patent Applications Nos. 10-2018-0067532 filed on Jun. 12, 2018 and 10-2019-0009232 filed on Jan. 24, 2019, each of which is hereby incorporated by reference.

TECHNICAL FIELD

The present disclosure relates to a robot arm structure applicable to a robot apparatus, and a manipulator of a surgical robot.

BACKGROUND ART

A surgical robot refers to a robot capable of performing surgical action on behalf of a surgeon who has performed the surgical action. Such a surgical robot may perform accurate and precise operations as compared with human beings and may perform a remote surgery. Surgical robots that are currently being developed worldwide may include bone surgical robots, laparoscopic surgical robots, stereotactic surgical robots, etc.

A surgical robot device generally includes a master console and a slave robot. When an operator manipulates a manipulation lever (e.g., a handle) provided on the master console, an instrument that is coupled to a robot arm of the slave robot or held by the robot arm is manipulated to perform a surgery.

The information in the background art described above was obtained by the inventors for the purpose of developing the present disclosure or was obtained during the process of developing the present disclosure. As such, it is to be appreciated that this information did not necessarily belong to the public domain before the patent filing date of the present disclosure.

DESCRIPTION OF EMBODIMENTS

Technical Problem

The present disclosure relates to a robot arm structure that is easy to operate and has improved safety by reducing collision during driving, and a manipulator of a surgical robot including the robot arm structure.

Solution to Problem

According to an embodiment of the present disclosure, a robot arm structure includes a first robot arm unit and a second robot arm unit, wherein the first robot arm unit includes: a plurality of first link arms; a first joint unit mounted on the first link arms and rotating the first link arms connected to each other about a first axis; and a second joint unit installed on at least one of the plurality of first link arms to adjust a length of the at least one link arm, and the second robot arm unit includes: a second link arm connected to the first link arms; a third joint unit using a lengthwise direction of the second link arm as a first rotary shaft and rotating the second link arm; and a fourth joint unit arranged on an end portion of the second link arm and rotating about a second rotary shaft that is perpendicular to the first rotary shaft.

Advantageous Effects of Disclosure

A robot arm structure and a manipulator of a surgical robot including the robot arm structure according to the present disclosure allow an instrument provided on an end portion to be movable. In particular, a user may allow the instrument to perform a linear movement, a yaw movement, and a pitch movement in a three-dimensional space by manipulating the robot arm structure.

Because the robot arm structure and the manipulator of the surgical robot including the robot arm structure according to the present disclosure have redundant degrees of freedom, a posture of the robot arm structure may be changed in a state in which of the instrument is fixed at a location during driving. When the robot arm structure is applied to the surgical robot, a possibility of collision during surgery may be reduced by changing a posture of an active arm without changing a direction of a surgical tool. However, the scope of the disclosure is not limited to the above effects.

BEST MODE

Figure 1:
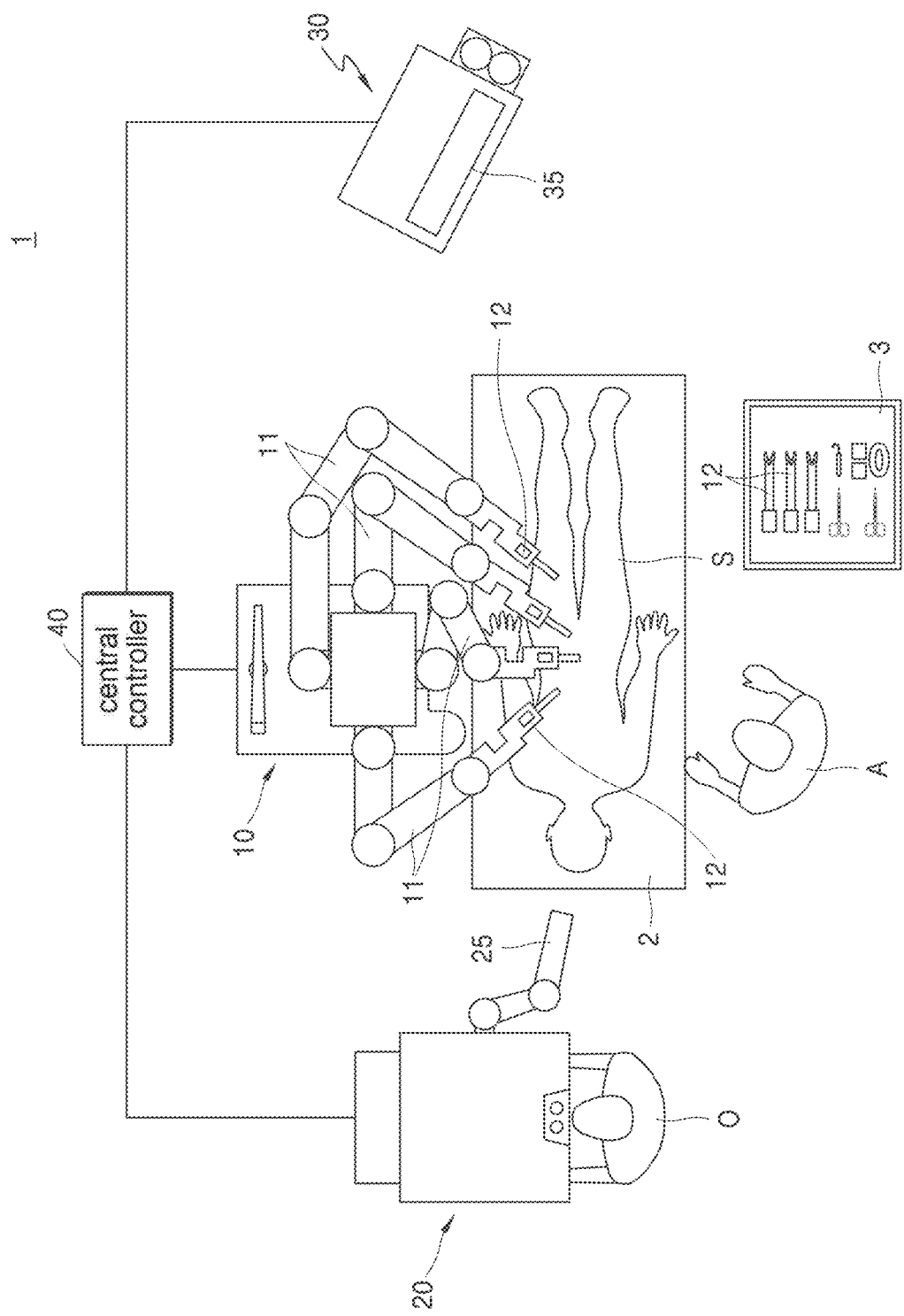
FIG. 1 is a plan view of an entire system of a surgical robot device according to an embodiment of the present disclosure.

According to an embodiment of the present disclosure, a robot arm structure includes a first robot arm unit and a second robot arm unit, wherein the first robot arm unit includes: a plurality of first link arms; a first joint unit mounted on one of the first link arms and rotating the one of the first link arms connected to each other about a first axis; and a second joint unit installed on at least one of the plurality of first link arms to adjust a length of the at least one link arm, and the second robot arm unit includes: a second link arm connected to the first link arms; a third joint unit using a lengthwise direction of the second link arm as a first rotary shaft and rotating the second link arm; and a fourth joint unit arranged on an end portion of the second link arm and rotating about a second rotary shaft that is perpendicular to the first rotary shaft.

The robot arm structure may further include an instrument installed at the end portion of the second link arm and being rotated by the fourth joint unit, wherein the first robot arm unit and the second robot arm unit may be driven to make the instrument perform a yaw movement or a pitch movement while maintaining a preset remote center of motion (RCM) point at a fixed location.

An extension line of the first rotary shaft and an extension line of the second rotary shaft may not pass through the RCM point.

The second robot arm unit may drive the third joint unit and the fourth joint unit and may set a yaw movement and a pitch movement of the instrument, and the first robot arm unit may drive the first joint unit and the second joint unit to maintain a position of the instrument fixed on the preset RCM point.

The second link arm may be connected to the first link arm so that the first rotary shaft has an inclination angle with respect to the first axis.

The inclination angle may be greater than 0° and less than 90°.

An end of the first robot arm unit may be fixed on a location in a three-dimensional space and an opposite end of the first robot arm unit may be connected to the second link arm.

At least one from the first joint unit to the fourth joint unit may provide the robot arm structure with redundant degrees of freedom to replace a movement of another joint unit.

The redundant degrees of freedom may allow the plurality of first link arms or the second link arm to move without changing a location and a direction of the instrument installed at the end portion of the second link arm.

One of the plurality of first link arms may have a first portion extending in a direction parallel to the ground and a second portion bent from the first portion to be in parallel with the first axis.

The second joint unit may include, a first linear motion joint that linearly moves along a second axis that is perpendicular to the first axis to move the second link arm; and a second linear motion joint that linearly moves along the first axis to move the second link arm.

The first link arms may include: a first link on which the first linear motion joint is installed; and a second link connected to the first link, having a portion bent along the second axis, and having the second linear motion joint installed on the portion, and the first joint unit may be installed on each of opposite ends of the first link or installed between the first link and the second link.

The first link arms may include: a first portion on which the first linear motion joint is installed; and a second portion connected to the first portion and bent along the second axis so that the second linear motion joint is installed.

According to another embodiment of the disclosure, a robot arm structure includes: a first rotating joint rotating about a first axis; a first link having an end connected to the first rotating joint; a first linear motion joint installed in the first link to adjust a length of the first link; a second rotating joint installed at an opposite end of the first link and rotating about the first axis; a second link having an end connected to the second rotating joint; a second linear motion joint installed in the second link and moving along the first axis; a third link connected to an opposite end of the second link and extending to have an inclination angle with respect to the first axis; a rolling joint installed in the third link and rotating about a first rotary shaft that is in a lengthwise direction of the third link; and a third rotating joint installed on an end portion of the third link and rotating about a second rotary shaft that is different from the first rotary shaft.

The robot arm structure may further include an instrument installed at an end portion of the third link and being rotated by the third rotating joint, wherein at least five joints from among the first rotating joint, the second rotating joint, the first linear motion joint, the second linear motion joint, the rolling joint, and the third rotating joint may be driven to make the instrument perform a yaw movement or a pitch movement while maintaining a preset remote center of motion (RCM) point at a fixed position.

At least one from the first rotating joint, the second rotating joint, the first linear motion joint, the second linear motion joint, the rolling joint, and the third rotating joint may provide the robot arm structure with redundant degrees of freedom to replace a movement of another joint.

The redundant degrees of freedom may allow at least one of the first link, the second link, and the third link to move without changing a location and a direction of the instrument installed at the end portion of the third link.

According to another embodiment of the disclosure, a manipulator of a surgical robot includes: a robot arm structure described above; and a passive arm structure connected to the robot arm structure and fixed when the robot arm structure is driven, wherein the passive arm structure includes: a first arm extending along the first axis; a third linear motion joint installed in the first arm and moving along the first axis to adjust a length of the first arm; a fourth rotating joint installed at an end portion of the first arm and rotating about the first axis; a second arm having an end connected to the fourth rotating joint; a fifth rotating joint installed at an opposite end of the second arm and rotating about the first axis; and a third arm having an end connected to the fifth rotating joint.

The passive arm structure may further include a fourth linear motion joint installed on at least one of the second arm and the third arm to adjust a length of the arm.

The manipulator may further include an instrument installed at an end portion of the robot arm structure, wherein the instrument may set a location of a remote center of motion (RCM) point by driving the passive arm structure and performs a yaw movement or a pitch movement by driving the robot arm structure while maintaining the RCM point at a fixed position.

Other aspects, features and advantages of the disclosure will become better understood through the accompanying drawings, the claims and the detailed description.

Mode of Disclosure

As the present disclosure allows for various changes and numerous embodiments, particular embodiments will be illustrated in the drawings and described in detail in the written description. However, this is not intended to limit the present disclosure to particular modes of practice, and it is to be appreciated that all modifications, equivalents, and/or alternatives that do not depart from the spirit and technical scope are encompassed in the disclosure. In describing the present disclosure, like reference numerals denote the same elements even when the elements are provided in another embodiment.

It will be understood that although the terms "first" and "second" are used herein to describe various elements, these elements should not be limited by these terms. Terms are only used to distinguish one element from other elements.

The terms used in the present specification are merely used to describe particular embodiments, and are not intended to limit the present disclosure. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, one or more embodiments will be described in detail with reference to accompanying drawings.

Hereinafter, a robot arm structure may be applied to various robots that are industrially available. The robot arm structure may be applied to various types of robot devices and robot systems, e.g., industrial robots, medical robots, mobile robots, etc.

That is, the robot arm structure according to the present disclosure is not limited to a certain shape, space, or purpose, and may be applied to various structures in which a plurality of links or arms are connected. However, an example in which the robot arm structure is installed in a surgical robot will be described below for convenience of description.

FIG. 1 is a plan view of an entire system of a surgical robot device 1 according to an embodiment of the present disclosure.

Referring to FIG. 1, the surgical robot device 1 may include a manipulator 10 performing surgery on a patient S lying on an operating table 2, and a master console 20 allowing an operator 0 to remotely control the manipulator 10. Also, the surgical robot device 1 may include a vision cart 30. An assistant A may check the progress of the surgery through a display unit 35 of the vision cart 30.

The manipulator 10 may include at least one robot arm 11. In general, a robot arm has a similar function to that of an arm and/or a wrist of a human being, and denotes a device having a wrist to which a certain tool may be attached. In the specification herein, the robot arm 11 may be defined as a concept encompassing such elements as an upper arm, a lower arm, a wrist, and an elbow, and a surgical instrument coupled to the wrist, etc. The robot arm 11 of the manipulator 10 as above may be implemented to operate with multiple degrees of freedom. The robot arm 11 may include an instrument 12 inserted into a surgical site of the patient S, a yaw driving unit for rotating the instrument 12 in a yaw direction according to the operating position, a pitch driving unit for rotating the instrument in a pitch direction that is perpendicular to the rotational driving of the yaw driving unit, a transport driving unit for moving the instrument 12 in a lengthwise direction, a rotation driving unit for rotating the instrument, and an instrument driving unit installed on an end of the instrument 12 to incise or cut a surgical lesion. However, the composition of the robot arm 11 is not limited thereto, and it is to be appreciated that such an example does not limit the scope of claims of the present disclosure Here, the actual control procedures by which the robot arm 11 is rotated, moved, etc., when the operator 0 manipulates a manipulation lever will not be described in detail.

One or more manipulators 10 may be used to operate the patient S, and the instrument 12 allowing the surgical site to be displayed as an image through the display unit 35 may be implemented as an independent manipulator 10. Also, as described above, the embodiments of the present disclosure may be universally used in surgeries in which various surgical endoscopes (e.g., thoracoscopy, arthroscopy, parenteral, etc.) other than laparoscopy are used.

The robot arm structure 100 may be applied to some of the robot arms 11 in the manipulator 10. Also, some other robot arms 11 may include passive arms 50. This will be described in detail later.

The master console 20 and the manipulator 10 are not necessarily provided as separate devices that are physically separated from each other, and may be combined and implemented integrally with each other. Hereinafter, a case in which the master console 20 and the manipulator 10 are physically separated from each other will be described below for convenience of description.

The master console 20 includes a manipulation lever (not shown) and a display unit (not shown). Also, the master console 20 may additionally include an external display apparatus 25 for displaying the status of the operator 0.

In detail, the master console 20 includes manipulation levers (not shown) that may be held and manipulated by both hands of the operator 0. The manipulation lever may include two or more handles, and a manipulation signal according to the handle manipulation of the operator 0 is transferred to the manipulator 10 through a wired or wireless communication network to control the robot arm 11. That is, surgical operations such as moving of a location, rotation, cut operation, etc. of the robot arm 11 may be performed by the operator 0 manipulating the handles.

For example, the operator 0 may manipulate the robot arm 11 or the instrument 12 by using the manipulation lever of a handle type. The manipulation lever as above may have various mechanical configurations according to the manipulation method thereof and may be provided in various types, for example, a master handle for manipulating operations of the slave robot arm 11 or the instrument 12, and various input units such as a joystick, a keypad, a trackball, or a touchscreen added to the master console 20 for manipulating functions of entire system, for operating the robot arm 11 of the manipulator 10 and/or other surgical instruments. Here, the manipulation lever is not limited to the shape of the handle, and may not be restricted to a certain shape provided that the manipulation lever has a shape capable of controlling operations of the robot arm 11 through a network such as a wired or wireless communication network.

An image captured by the instrument 12 is displayed on the display unit of the master console 20. Also, the display unit may display a certain virtual manipulation plate independently or together with the image captured by the instrument 12.

The display unit may be provided in various types by which the operator 0 may check the image. For example, the display apparatus may be provided to correspond to both eyes of the operator 0. In another example, the display unit may include one or more monitors such that information that is necessary during the surgery may be displayed on each monitor. The number of the display units may be determined depending on the type or kind of the information that needs to be displayed. The master console 20 will be described in more detail below.

The vision cart 30 is installed apart from the manipulator 10 or the master console 20, and the progress of the surgery may be checked through the display unit 35 from outside. The image displayed by the display unit 35 may be the same as the image displayed on the master console 20 of the operator 0. The assistant A may assist the surgery performed by the operator 0 while checking the image on the display unit 35. For example, the assistant A may replace the instrument 12 from an instrument cart 3 according to the progress of the surgery.

A central controller 40 is connected to the manipulator 10, the master console 20, and the vision cart 30 to receive/transmit signals from/to each of the manipulator 10, the master console 20, and the vision cart 30. The central controller 40 may be provided in one of the manipulator 10, the master console 20, and the vision cart 30, or may be independently provided.

Figure 2:
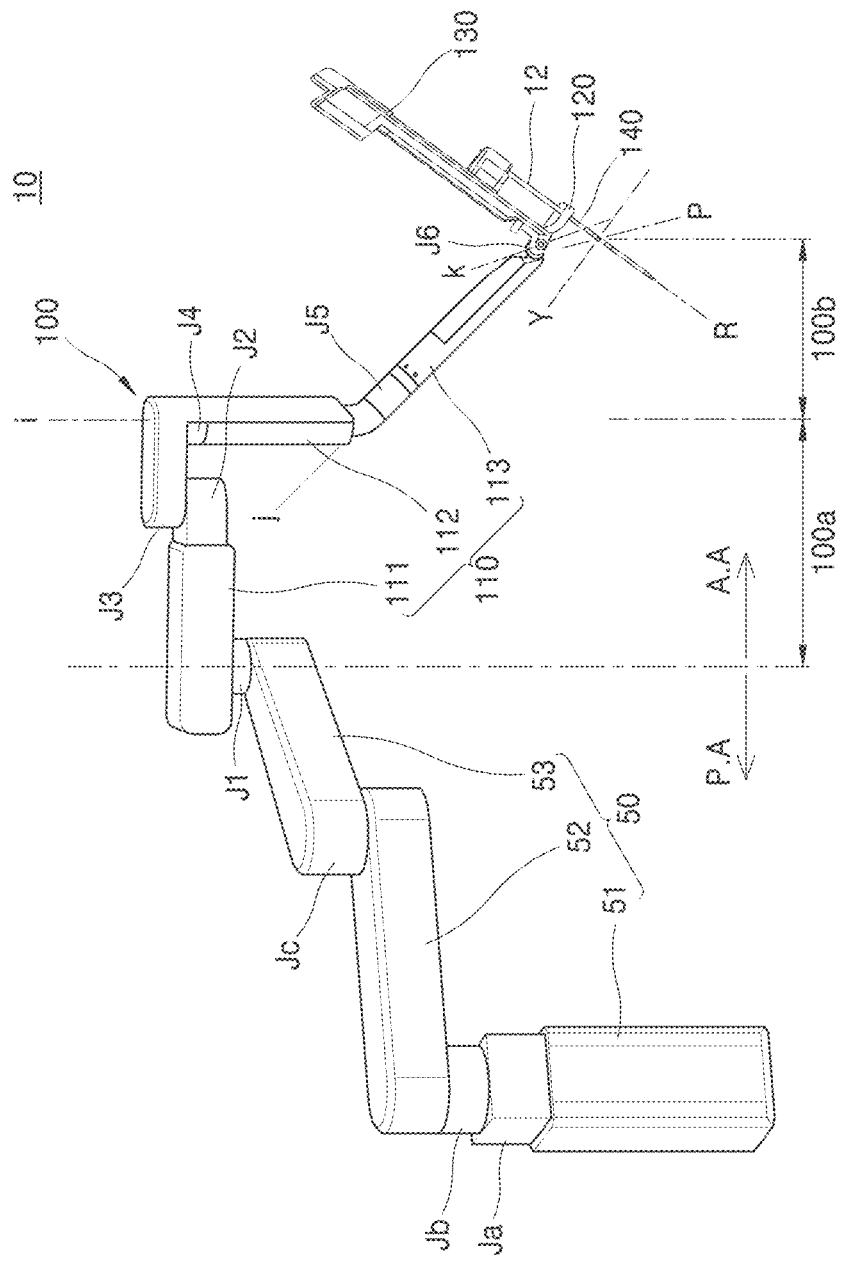
FIG. 2 is a perspective view of a manipulator in the surgical robot of FIG. 1.

FIG. 2 is a perspective view of the manipulator 10 in the surgical robot of FIG. 1.

Hereinafter, a first axis i is defined as an axis that is substantially perpendicular to the ground. When a joint rotates about the first axis i, spatial position of an arm or a link may be adjusted.

Also, the first axis i is defined as an axis crossing a center of each rotating joint, and there may be a plurality of first axes i according to the number of the rotating joints. That is, each of the rotating joints has a rotary shaft passing through the rotating center, and the rotary shafts are in parallel with one another according to locations of the rotating joints. Therefore, the first axis i is defined to include a plurality of rotary shafts that are substantially perpendicular to the ground and in parallel with one another and defined as a concept including parallel shafts.

In detail, referring to FIG. 2, a first rotating joint J1, a second rotating joint J3, a fourth rotating joint Jb, and a fifth rotating joint Jc may rotate about the first axes i that pass through respective rotating centers and are parallel to one another. Also, a second linear motion joint J4 and a third linear motion joint Ja may linearly move based on the first axes i.

Referring to FIG. 2, the manipulator 10 of the surgical robot may be classified as a passive area P.A and an active area A.A. The passive area P.A and the active area A.A are divided according to driving ranges of the surgical robot device 1 during the surgery.

In detail, the passive arm 50 is installed in the passive area P.A in which the passive arm 50 is only driven before the surgery, and an active arm 100 is not driven at this time. The passive area P.A is an area for setting the position of the surgical robot device 1 before performing the surgery, and the operator 0 or the assistant A operates the passive arm 50 to set the position of the active arm 100.

The passive arm 50 may move the active arm 100 to a desired position in a surgery preparation process, but is not moved at a fixed location during the surgery. The passive arm 50 includes a plurality of joints and arms or links for connecting the joints. Each of the joints makes a rotation movement or a prismatic movement, and a total movement of the passive arm 50 is generated through the movements. The joint may include an actuator, a reducer, a sensor, a brake, a counterbalance, etc.

The actuator mainly includes an electrical motor. e.g., a brushed DC (BDC) motor, a brushless DC (BLDC) motor, an AC motor, etc. The reducer may be implemented as a gear such as a harmonic drive, a planetary gear, etc. The sensor may include an encoder, a resolver, etc. for measuring the movement of the joint and may include a force/torque sensor for measuring force or torque applied to a link connected to each joint. The brake is a device for restricting the movement of the joint and includes a solenoid, a spring, etc. as main elements. In addition, the brake may be configured as a type that is connected to the actuator to restrict the movement of the actuator, a type connected to the link to restrict the movement of the link, or both of the two types. The counterbalance is a device that compensates for a weight of the robot arm and exerts a force for offsetting the weight of the robot arm in a static state.

The passive arm 50 includes a first arm 51, a second arm 52, and a third arm 53 connected to one another and may also include three joints. The passive arm 50 adjusts three links by using three joints so as to move to a desired position in a three-dimensional space.

The first arm 51 may extend in the first axis i. In the first arm 51, a third linear motion joint Ja that adjusts a length of the first arm 51 in the first axis i may be provided. That is, the first arm 51 is installed perpendicularly to the ground and has the third linear motion joint Ja arranged therein so as to linearly move in the direction perpendicular to the ground. As such, the passive arm 50 may adjust the height of the active arm 100.

The fourth rotating joint Jb that rotates about the first axis i may be installed at an end portion of the first arm 51. The fourth rotating joint Jb connects the first arm 51 to the second arm 52 and allows the second arm 52 to rotate about the first axis i with respect to the first arm 51.

The second arm 52 is connected to the first arm 51 to be rotatable with respect to the first arm 51. The first arm 51 and the second arm 52 are substantially perpendicular to each other, but are not limited thereto, that is, may have an angle ranging from +15° to −15° therebetween.

The second arm 52 has an end connected to the fourth rotating joint Jb. The second arm 52 is connected to the first arm 51 via the fourth rotating joint Jb, and thus may rotate about the first axis i with respect to the first arm 51. In an embodiment, the second arm 52 extends in a direction parallel to the ground and thus may be substantially perpendicular to the first arm 51.

The third arm 53 is connected to the second arm 52 to be rotatable with respect to the second arm 52. The second arm 52 and the third arm 53 are substantially parallel to each other, but are not limited thereto, that is, may have an angle ranging from +15° to −15° therebetween.

The third arm 53 has an end connected to the fifth rotating joint Jc. The third arm 53 is connected to the second arm 52 via the fifth rotating joint Jc, and thus, may rotate about the first axis i with respect to the second arm 52. In an embodiment, the third arm 53 is arranged parallel to the ground, like the second arm 52.

The active arm 100 is installed in the active area A.A. The active arm 100 is only driven during the surgery in the active area A.A, and the passive arm 50 is not driven. When the active arm 100 is driven in the active area A.A, the instrument 12 may perform the surgery with a plurality of degrees of freedom. That is, the active area A.A is a part driven during the surgery, and the operator 0 manipulates the master console to drive the instrument 12. Here, the instrument 12 may perform a yaw movement, a pitch movement, and a roll movement while maintaining a state of being fixed to a remote center of motion (RCM) set in advance.

The active arm 100 has the instrument 12 or an endoscope (not shown) at an end portion thereof, and each joint in the active arm 100 is driven during the surgery so that the instrument 12 or the endoscope may move in the patient's body. The active arm 100 includes a plurality of joints and arms or links connecting the joints. Each of the joints performs a rotation movement or prismatic movement, and the active arm 100 entirely moves through the movement. The joint may include an actuator, a reducer, a sensor, a brake, a counterbalance, etc. A configuration of each joint is substantially the same as that of the passive arm 50, and operations according to the arrangement are different from those of the passive arm 50 and thus will be described in detail below.

Figure 3:
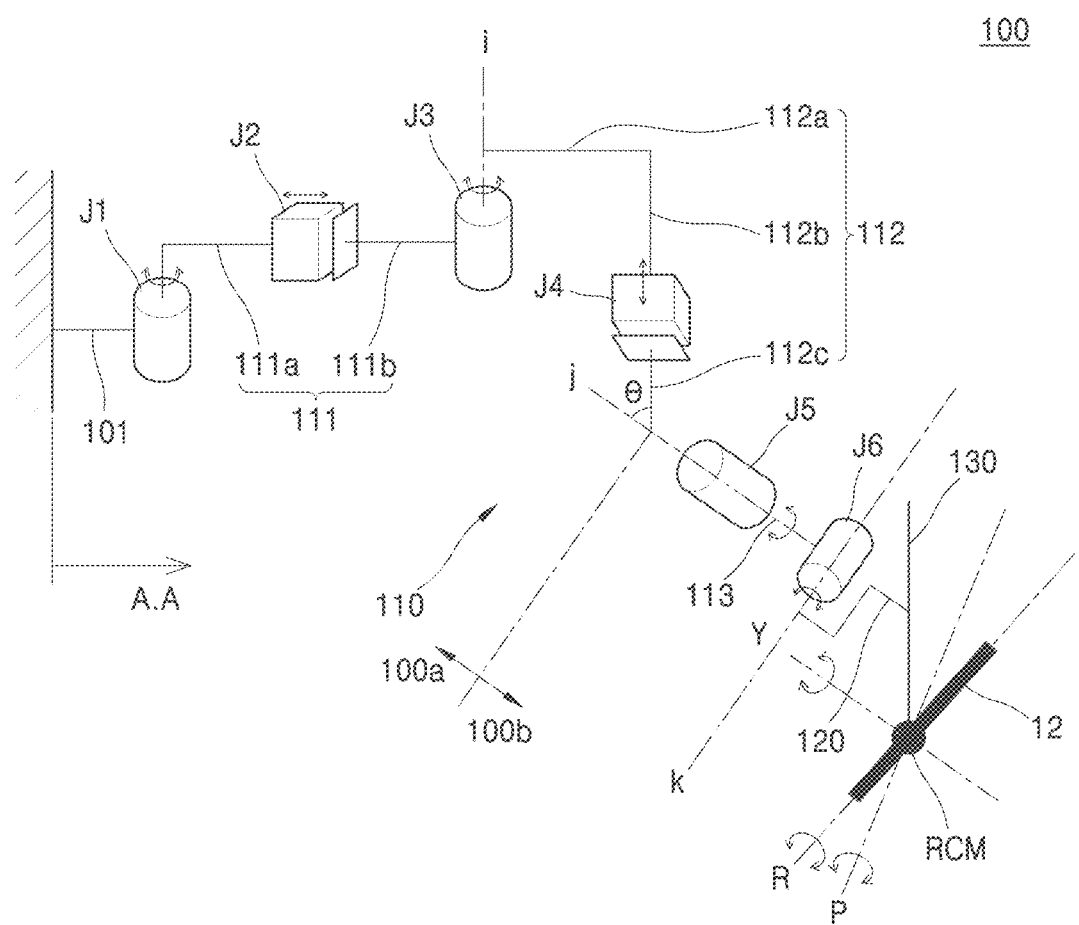
FIG. 3 is a diagram showing a robot arm structure according to an embodiment of the present disclosure.
Figure 4:
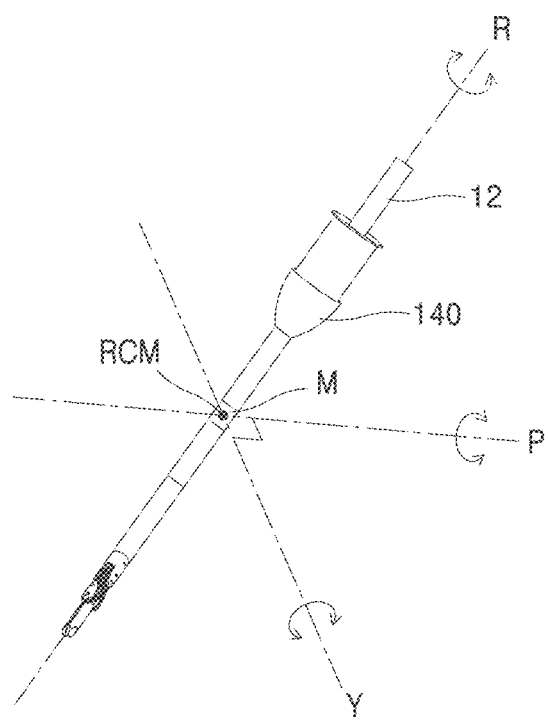
FIG. 4 is a perspective view of an instrument that may be provided in FIG. 3.

FIG. 3 is a diagram of a robot arm structure 100 according to an embodiment, and FIG. 4 is a perspective view of the instrument 12 that may be provided in FIG. 3.

The robot arm structure 100 according to the embodiment may be installed in the active area A.A. Therefore, the robot arm structure 100 may be applied as an active arm when being used in a surgical robot device. Therefore, the robot arm structure and the active arm will be used interchangeably hereinafter.

Referring to FIGS. 2 to 4, the robot arm structure 100 includes a plurality of links and joints, and a cannula holder 120, a slider guide 130, and a cannula 140 may be installed at an end portion of the robot arm structure 100. The robot arm structure 100 may be defined only by the plurality of links and joints or may be defined to include the cannula holder 120, the slider guide 130, and the cannula 140.

The plurality of links may include a first link 111, a second link 112, and a third link 113. The plurality of links may have an angle ranging from +15° to −15° therebetween. The plurality of links may be connected to one another by the first rotating joint J1, a first linear motion joint J2, the second rotating joint J3, the second linear motion joint J4, a rolling joint J5, and a third rotating joint J6.

The first link 111 includes an end 111a and an opposite end 111b connected to the first linear motion joint J2. The end 111a of the first link 111 is connected to the first rotating joint J1 The first rotating joint J1 may rotate about the first axis i. Because the first rotating joint J1 is connected to a fixed link 101, the first link 111 rotates about the first axis i with respect to the fixed link 101.

The fixed link 101 is a portion having a fixed position in a three-dimensional space and is not limited to a certain name and location. In an embodiment, the fixed link 101 may be the third arm 53 of the passive arm 50. Hereinafter, a case in which the fixed link 101 is the third arm 53 will be described.

The first linear motion joint J2 is installed in the first link 111 to adjust a length of the first link 111. Lengths of the end 111a and the opposite end 111b of the first link 111 may be adjusted by the first linear motion joint J2. The first linear motion joint J2 may perform the prismatic movement. The length of the first link 111 may be adjusted by adjusting the first linear motion joint J2.

The second rotating joint J3 that rotates about the first axis i may be installed at the opposite end 111b of the first link 111. The second rotating joint J3 may connect the first link 111 to the second link 112, and thus the first link 111 and the second link 112 may rotate about the first axis i.

The second link 112 includes a first end portion 112a, a middle portion 112b, and a second end portion 112c The second link 112 is connected to the first link 111 via the second rotating joint J3 and has the second linear motion joint J4 installed therein so that a length in a height direction thereof may be adjusted.

The first end portion 112a is connected to the second rotating joint J3 to rotate about the first axis i. The middle portion 112b is bent from the first end portion 112a in the first axis i direction. The middle portion 112b extends in the first axis i direction and has the second linear motion joint J4 therein to be linearly moved in the first axis i direction. The second end portion 112c is connected to the second linear motion joint J4 and may be connected to the third link 113.

The second link 112 is bent such that the first end portion 112a and the middle portion 112b are substantially perpendicular to each other. The second linear motion joint J4 is installed in the middle portion 112b and moves along the first axis i to adjust the height of the instrument 12.

The third link 113 is connected to an opposite end of the second link 112, that is, the second end portion 112c, and extends to have an inclination angle (e) with respect to the first axis i. The third link 113 forms one body with the second end portion 112c and is bent from the second link 112. Because the second end portion 112c extends in the first axis i direction, a first rotary shaft j in the lengthwise direction of the third link 113 and the first axis i in the lengthwise direction of the second end portion 112c may have an inclination angle θ therebetween. For example, the inclination angle θ may be greater than 0° and less than 90°.

The rolling joint J5 may be installed in the third link 113. The rolling joint J5 may rotate about the first rotary shaft j that is the lengthwise direction of the third link 113. Because the third link 113 is bent from the second link 112, the first rotary shaft j may form the inclination angle θ with respect to the first axis i.

The rolling joint J5 may generate a roll movement of the third link 113. The roll movement of the rolling joint J5 may cause a yaw movement of the instrument 12. The inclination angle θ is arranged in a direction similar to that of a yaw axis Y of the instrument 12 so as to generate the yaw movement of the instrument 12. That is, when rotating the rolling joint J5, the instrument 12 may rotate about the yaw axis Y. However, because an extension line of the first rotary shaft j does not pass through the RCM point, the location of the instrument 12 may change when the rolling joint J5 rotates. However, the location of the instrument 12 may be corrected by driving another joint so that the instrument 12 may maintain the RCM point. This will be described in detail later.

The third rotating joint J6 may be installed at an end portion of the third link 113. The third rotating joint J6 rotates about a second rotary shaft k, and the second rotary shaft k may be perpendicular to the first rotary shaft j in a three-dimensional space.

When the third rotating joint J6 rotates about the second rotary shaft k, a pitch movement of the instrument 12 may be generated. The second rotary shaft k is arranged in a direction similar to a pitch axis P of the instrument 12 so as to generate the pitch movement of the instrument 12. That is, when the third rotating joint J6 rotates, the instrument 12 may rotate about the pitch axis P. However, because an extension line of the second rotary shaft k does not pass through the RCM point, the location of the instrument 12 may change when the third rotating joint J6 rotates. However, the location of the instrument 12 may be corrected by driving another joint so that the instrument 12 may maintain the RCM point. This will be described in detail later.

The robot arm structure 100 may perform the yaw movement or the pitch movement in a state in which the RCM point of the instrument 12 is maintained at a fixed location. In the robot arm structure 100, the RCM point of the instrument 12 may be maintained via software. When the first rotating joint J1, the first linear motion joint J2, the second rotating joint J3, the second linear motion joint J4, the rolling joint J5, and the third rotating joint J6 are driven, the instrument 12 may perform the yaw movement, the pitch movement, and the rolling movement while maintaining a constant location from the RCM point.

The instrument 12 may have at least five degrees of freedom by driving the first rotating joint J1, the first linear motion joint J2, the second rotating joint J3, the second linear motion joint J4, the rolling joint J5, and the third rotating joint J6. To this end, at least five joints from among the plurality of joints may be driven. The instrument 12 may perform the linear movement in three directions, the yaw movement, and the pitch movement.

At least one of the first rotating joint J1, the first linear motion joint J2, the second rotating joint J3, the second linear motion joint J4, the rolling joint J5, and the third rotating joint J6 provides the robot arm structure 100 with redundant degrees of freedom to thereby replace the movement of other joints. The robot arm structure 100 uses five joints in order to implement five degrees of freedom, and the remaining one joint may provide redundant degrees of freedom.

The redundant degrees of freedom may allow at least one of the first link 111, the second link 112, and the third link 113 to move without changing the location and direction of the instrument 12 installed at the end portion of the third link 113. As such, one of the links in the robot arm structure 100 may be moved while performing a surgical operation by using the instrument 12, and thus, robot arms may be prevented from spatially interfering with each other.

The cannula holder 120 is installed at the end portion of the third link 113 and the cannula 140 may be mounted therein. The slider guide 130 is also installed at the end portion of the third link 113 and may guide the prismatic movement of the instrument 12.

Referring to FIG. 4, the instrument 12 is installed in the cannula 140 to be mounted in the robot arm structure 100. The instrument 12 may perform the yaw movement, the pitch movement, and the roll movement while maintaining the fixed position at the preset RCM point during the surgery.

The RCM point is fixed at a location during the surgery and is placed on an incision part of a patient. Because the RCM point is placed on the incision part of the patient, the surgery may be performed with minimal invasiveness. The RCM point is indicated on an outer side of the cannula 140 with a marker M such that the operator 0 or the assistant A may easily recognize and set the surgical robot device 1 for performing the surgery.

The instrument 12 may perform the yaw movement, the pitch movement, and the roll movement at the fixed RCM point. The roll movement may be performed when the instrument 12 performs the roll movement, but the yaw movement and the pitch movement may be performed by the driving of the robot arm structure 100.

Also, the instrument 12 may move in the three-dimensional space to the RCM point. Movements of the instrument 12 in an X-axis, a Y-axis, and a Z-axis may be performed by the driving of the robot arm structure 100.

That is, prismatic movements in the X-axis direction, Y-axis direction, and Z-axis direction, the yaw movement, and the pitch movement of the instrument 12 are performed by the driving of the robot arm structure 100.

In another embodiment, the robot arm structure 100 may be classified as a first robot arm unit 100a and a second robot arm unit 100b based on a region affecting the operation of the instrument 12. The first robot arm unit 100a includes a first link arm, a first joint unit, and a second joint unit, and the second robot arm unit 100b includes a second link arm, a third joint unit, and a fourth joint unit.

An end portion of the first robot arm unit 100a is fixed at a location in a three-dimensional space, and an opposite end of the first robot arm unit 100a is connected to the second link arm of the second robot arm unit 100b.

There may be a plurality of first link arms including the first link 111 and the second link 112. The first linear motion joint J2 is installed on the first link 111. In addition, the second link 112 is connected to the first link 111 and may be partially bent in a second axis that is perpendicular to the first axis i. The second linear motion joint J4 may be installed on a part of the second link 112. One of the first link arms may include a first portion extending in a direction parallel to the ground and a second portion bent from the first portion to be parallel to the first axis i. That is, the first end portion 112a of the second link 112 extends in parallel with the ground, and the middle portion 112b and the second end portion 112c of the second link 112 may extend along the first axis i.

The first joint unit is provided between the first link arms so as to rotate the first link arms connected thereto about the first axis i. The first joint unit may include the first rotating joint J1 and the second rotating joint J3 that are respectively installed at opposite ends of the first link 111.

The second joint unit is installed on at least one of the plurality of first link arms to adjust a length of the first link arm. The second joint unit may include the first linear motion joint J2 and the second linear motion joint J4 that linearly move in different directions from each other. The first linear motion joint J2 linearly moves along the second axis that is perpendicular to the first axis i to move the second link arm, and the second linear motion joint J4 linearly moves along the first axis i to move the second link arm.

The first robot arm unit 100a has a function of setting a location of the instrument 12 in the three-dimensional space by driving the first joint unit and the second joint unit and a function of correcting the yaw movement and the pitch movement of the instrument 12.

When the first rotating joint J1, the second rotating joint J3, the first linear motion joint J2, and the second linear motion joint J4 are driven, the location of the instrument 12 in the three-dimensional space may be changed Therefore, the first joint unit and the second joint unit may be driven to change the spatial location of the instrument 12.

Also, the first joint unit and the second joint unit may be driven so as to maintain the RCM point of the instrument 12 while the instrument 12 performs the yaw movement and the pitch movement. When the spatial location of the instrument 12 is changed during the yaw movement and the pitch movement of the instrument 12 due to the driving of the second robot arm unit 100b, the first and second joint units may be driven to correct the location of the instrument 12.

The second robot arm unit 100b is connected to the first robot arm unit 100a and has the instrument 12 mounted on an end portion thereof. The instrument 12 is installed at the end portion of the second link arm and may be rotated by the fourth joint unit.

The second link arm is connected to the first link arm and corresponds to the third link 113. In the second link arm, the first rotary shaft j extending in the lengthwise direction may have the inclination angle θ with respect to the first axis i.

The third joint unit has the lengthwise direction of the second link arm as a first rotary shaft thereof and may rotate the second link arm. The third joint unit corresponds to the rolling joint J5 and may rotate about the first rotary shaft j.

The fourth joint unit is arranged at the end portion of the second link arm and may rotate about the second rotary shaft k that is perpendicular to the first rotary shaft j. The fourth joint unit corresponds to the third rotating joint J6 and may rotate about the second rotary shaft k that is perpendicular to the first rotary shaft j and the first axis i.

The second robot arm unit 100b has a function of setting the yaw movement and the pitch movement of the instrument 12 by driving the third joint unit and the fourth joint unit and a function of correcting the location of the instrument 12 in the three-dimensional space.

Because the first rotary shaft j is in parallel with the yaw axis Y of the instrument 12, when the rolling joint J5 rotates about the first rotary shaft j, the instrument 12 may perform the yaw movement. However, because the first rotary shaft j does not pass through the RCM point, the location of the instrument 12 in the three-dimensional space is changed even when the rolling joint J5 of the third link 113 is driven. That is, the rolling joint J5 has the function of generating the yaw movement of the instrument 12 as a main function thereof, but may also have a function of changing the location of the instrument 12 in the three-dimensional space as a sub-function.

Because the second rotary shaft k is in parallel with the pitch axis P of the instrument 12, when the third rotating joint J6 rotates about the second rotary shaft k, the instrument 12 may perform the pitch movement. However, the second rotary shaft k does not pass through the RCM point, and thus, even when the third rotating joint J6 is driven, the location of the instrument 12 in the three-dimensional space is changed. That is, the third rotating joint J6 has the function of generating the pitch movement of the instrument 12 as a main function thereof, but at the same time, also has a function of changing the location of the instrument 12 in the three-dimensional space as a sub-function.

The location change caused by the driving of the third and fourth joint units in the second robot arm unit 100b may be corrected by driving the first and second joint units in the first robot arm unit 100a. As such, the instrument 12 may perform the yaw movement or the pitch movement while maintaining the location thereof fixed at the preset RCM point.

The robot arm structure 100 may have redundant degrees of freedom. At least one of the first to fourth joint units provides the other joint units with the redundant degrees of freedom so as to replace the movement of the other joint units. That is, the redundant degrees of freedom may allow the plurality of first link arms or the second link arm to move without changing the location and direction of the instrument 12 installed at the end portion of the second link arm.

Because the robot arm structure 100 has the redundant degrees of freedom, the arrangement of the robot arm may be easily set during the surgery. One link is allowed to move due to the redundant degrees of freedom, and thus, the location of the link is moved during the surgery to overcome the spatial limitation.

The robot arm structure 100 and the manipulator 10 of the surgical robot including the robot arm structure 100 according to the present disclosure allow the instrument 12 installed at the end portion to move. In particular, the user may allow the instrument 12 to perform the prismatic movement, the yaw movement, and the pitch movement in the three-dimensional space by manipulating the robot arm structure 100.

Because the robot arm structure 100 and the manipulator 10 of the surgical robot including the robot arm structure 100 according to the present disclosure have redundant degrees of freedom, a posture of the robot arm structure 100 may be changed in a state in which a location of the instrument is fixed during driving. When the robot arm structure 100 is applied to the surgical robot, a possibility of collision during the surgery may be reduced by changing a posture of an active arm without changing the direction of the surgical tool.

Figure 5:
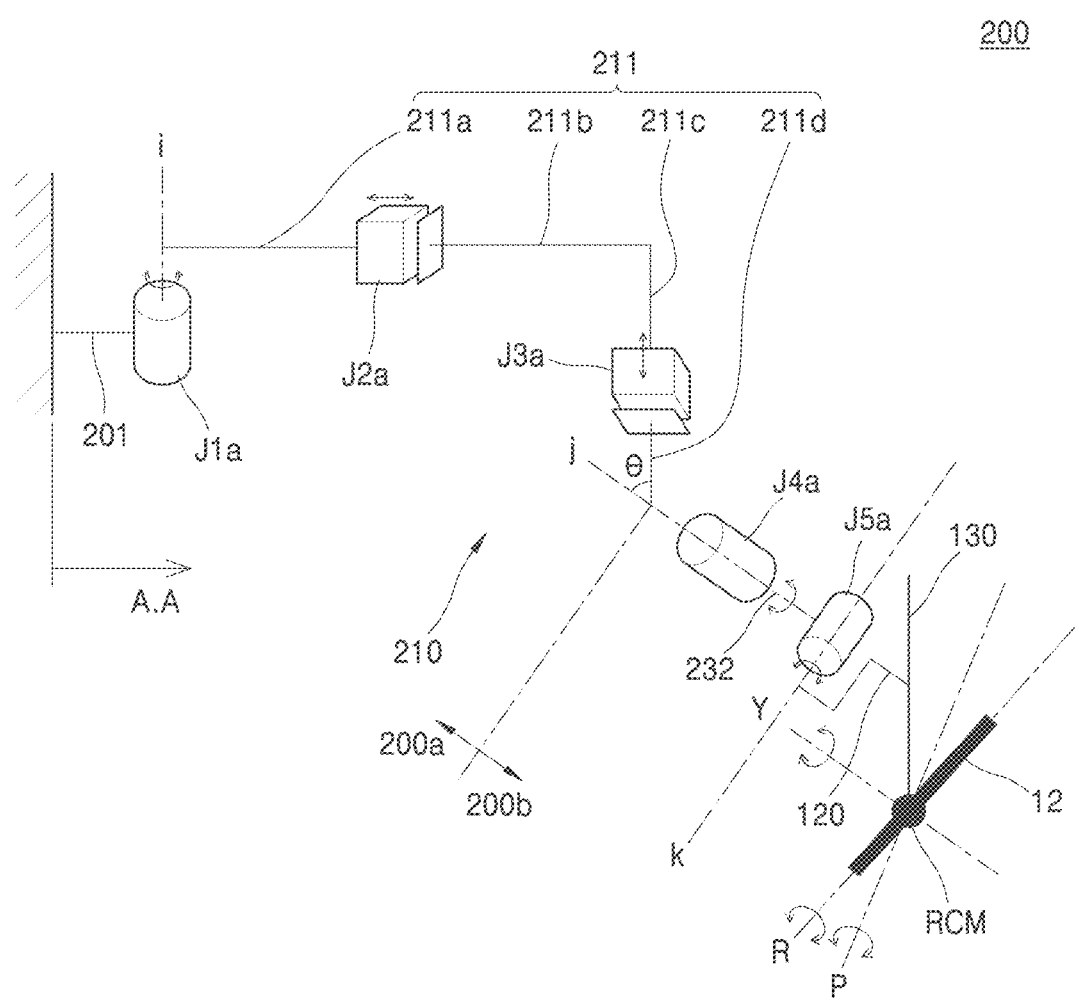
FIG. 5 is a diagram showing a robot arm structure according to another embodiment of the present disclosure.

FIG. 5 is a diagram of a robot arm structure 200 according to another embodiment of the present disclosure.

Referring to FIG. 5, the robot arm structure 200 includes a plurality of links and joints and may allow the instrument 12 installed at an end portion thereof to move. As compared with the robot arm structure 100 according to the previous embodiment, the number of joints is reduced and a shape of the link is changed according to the robot arm structure 200. Hereinafter, the differences will be described below.

The robot arm structure 200 may include a first robot arm unit 200a and a second robot arm unit 200b.

The first robot arm unit 200a may include a first link arm 211, a first joint unit J1a, and a second joint unit. The first robot arm unit 200a includes one link that is bent, one rotating joint, and two linear motion joints.

The first link arm 211 includes a first end 211a, a first middle-end 211b, a second middle-end 211c, and a second end 211d. The first end 211a is connected to a fixed link 201 via the first joint unit J1a. The first end 211a and the first middle-end 211b are connected to each other via a first linear motion joint J2a. The second middle-end 211c is bent from the first middle-end 211b in the first axis i direction. A second linear motion joint J3a may be installed between the second middle-end 211c and the second end 211d.

The second robot arm unit 200b may include a second link arm 232, a third joint unit J4a, and a fourth joint unit J5a. Because the second robot arm unit 200b is substantially the same as the second robot arm unit 100b in the above-described embodiment, detailed descriptions thereof are omitted.

The robot arm structure 200 according to the present disclosure allows the instrument 12 installed at the end portion thereof to move. In particular, the user may allow the instrument 12 to perform the prismatic movement, the yaw movement, and the pitch movement in the three-dimensional space by manipulating the robot arm structure 200.

Figure 6:
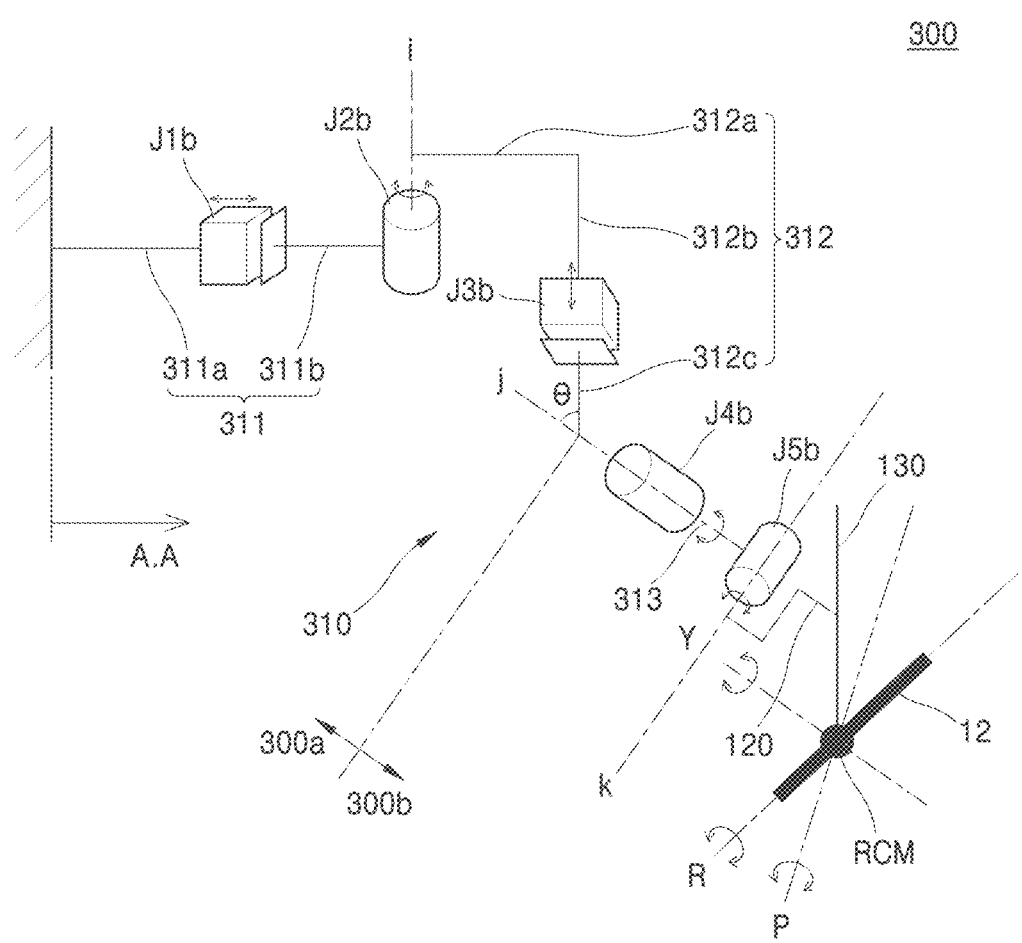
FIG. 6 is a diagram showing a robot arm structure according to another embodiment of the present disclosure.

FIG. 6 is a diagram of a robot arm structure 300 according to another embodiment of the present disclosure.

Referring to FIG. 6, the robot arm structure 300 includes a plurality of links and joints and may allow the instrument 12 installed on an end portion thereof to move. As compared with the robot arm structure 100 according to the above-described embodiment, the number of joints is reduced and a shape of the link is changed according to the robot arm structure 300. Hereinafter, the differences will be described below.

The robot arm structure 300 may include a first robot arm unit 300a and a second robot arm unit 300b.

The first robot arm unit 300a may include a first link arm, a first joint unit J2b, and a second joint unit. The first robot arm unit 300a includes a plurality of links, one rotating joint, and two linear motion joints.

The first link arm may include a first link 311 extending in one direction, and a second link 312 bent from the first link 311. The first link 311 may include an end 311a connected to an external structure, and an opposite end 311b connected to the first joint unit J2b. For example, the end 311a is fixed at an end portion of the passive arm 50. The first linear motion joint J1b connects the end 311a and the opposite end 311b to each other and may adjust the length.

The second link 312 includes a first end portion 312a, a middle portion 312b, and a second end portion 312c. The first end portion 312a is connected to the first link 311, and the middle portion 312b has a second linear motion joint J3b installed thereon to adjust the height of the instrument 12. The second end portion 312b may be connected to a second link arm 313. The second link 312 is substantially the same as the second link 112 in the above-described embodiment.

The second robot arm unit 300b may include the second link arm 313, a third joint unit J4b, and a fourth joint unit J5b. Because the second robot arm unit 300b is substantially the same as the second robot arm unit 100b in the above-described embodiment, detailed descriptions thereof are omitted.

The robot arm structure 300 according to the present disclosure allows the instrument 12 installed at the end portion thereof to move. In particular, the user may allow the instrument 12 to perform the prismatic movement, the yaw movement, and the pitch movement in the three-dimensional space by manipulating the robot arm structure 300.

Figure 7:
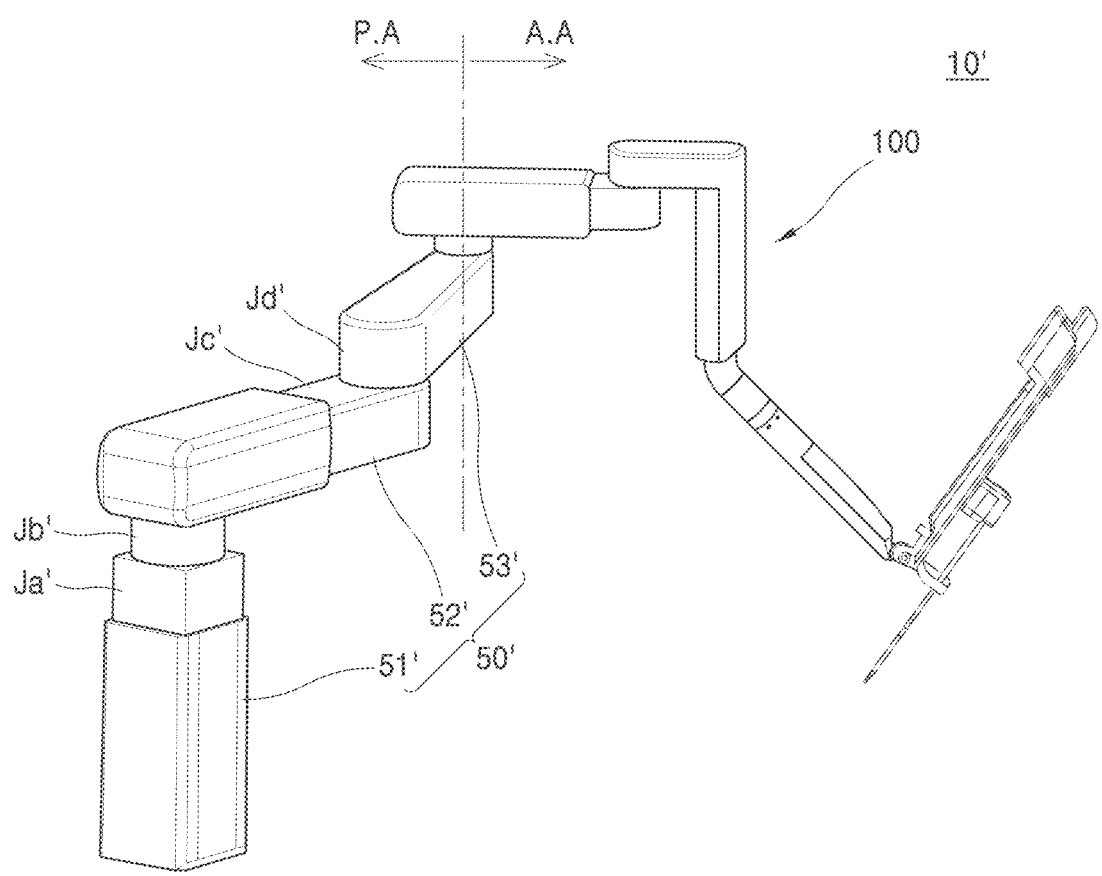
FIG. 7 is a perspective view of a manipulator in the surgical robot of FIG. 2, according to another embodiment of the present disclosure.

FIG. 7 is a perspective view of a manipulator 10' in the surgical robot of FIG. 2, according to another embodiment.

Referring to FIG. 7, in the manipulator 10' of the surgical robot, a passive arm 50' may have redundant degrees of freedom. The manipulator 10' includes the passive arm 50' and an active arm, and the robot arm structure 100, 200, or 300 may be applied to the active arm.

The passive arm 50' includes a first arm 51', a second arm 52', and a third arm 53' connected to one another and may also include four joints. The passive arm 50' adjusts three links by using four joints so as to move to a desired position in a three-dimensional space.

The first arm 51' may extend along the first axis i. In the first arm 51', a third linear motion joint Ja' that adjusts a length of the first arm 51' may be provided in the first axis i direction. That is, the first arm 51' is installed perpendicularly to the ground and has the third linear motion joint Ja' arranged therein so as to perform prismatic movement in the direction perpendicular to the ground. As such, the passive arm 50' may adjust the height of the active arm 100.

A fourth rotating joint Jb' that rotates about the first axis i may be installed at an end portion of the first arm 51'. The fourth rotating joint Jb' connects the first arm 51' to the second arm 52' and allows the second arm 52 to rotate about the first axis i.

The second arm 52' is connected to the first arm 51' to be rotatable with respect to the first arm 51'. The first arm 51' and the second arm 52' are substantially perpendicular to each other, but are not limited thereto, that is, may have an angle ranging from +15° to −15° therebetween.

The second arm 52' has an end connected to the fourth rotating joint Jb'. The second arm 52' is connected to the first arm 51' via the fourth rotating joint Jb', and thus may rotate about the first axis i with respect to the first arm 51'. In an embodiment, the second arm 52' extends in a direction parallel to the ground, and thus may be substantially perpendicular to the first arm 51'.

In the second arm 52', a fourth linear motion joint Jc' adjusting a length of the second arm 52' may be installed. The fourth linear motion joint Jc' may adjust the length of the second arm 52'.

The third arm 53' is connected to the second arm 52' to be rotatable with respect to the second arm 52'. The second arm 52' and the third arm 53' are substantially parallel to each other, but are not limited thereto, that is, may have an angle ranging from +15, to −15° therebetween.

The third arm 53' has an end connected to a fifth rotating joint Jd'. The third arm 53' is connected to the second arm 52' via the fifth rotating joint Jd', and thus may rotate about the first axis i with respect to the second arm 52' In an embodiment, the third arm 53' is arranged parallel to the ground like the second arm 52'.

In another embodiment, the fourth linear motion joint Jc' may be installed in the third arm 53'. The fourth linear motion joint Jc' may adjust the length of the third arm 53'.

The robot arm structure 100 and the manipulator 10' of the surgical robot including the robot arm structure 100 according to the present disclosure allow the instrument 12 installed at the end of the robot arm structure 100 to move. In particular, the user may allow the instrument 12 to perform the prismatic movement, the yaw movement, and the pitch movement in the three-dimensional space by manipulating the robot arm structure 100.

Because the robot arm structure 100 and the manipulator 10' of the surgical robot including the robot arm structure 100 according to the present disclosure have redundant degrees of freedom, a posture of the robot arm structure 100 may be changed in a state in which a location of the instrument 12 is fixed during driving. When the robot arm structure 100 is applied to the surgical robot, a possibility of collision may be reduced by changing a posture of an active arm without changing the direction of the surgical tool during the surgery.

While the disclosure has been described with reference to exemplary embodiments thereof, it will be understood by those of ordinary skill in the art that various changes in form and details may be made therein without departing from the spirit and scope of the disclosure. Although not described, it would be appreciated that equivalent units may be coupled to the disclosure Therefore, the scope sought to be protected of the disclosure shall be defined by the appended claims.

INDUSTRIAL APPLICABILITY

According to an embodiment of the present disclosure, a robot arm structure may be applied to various robot devices that may be industrially applicable. The robot arm structure may be applied to various types of robot devices and robot systems, e.g., industrial robots, medical robots, mobile robots, etc.

In particular, one or more embodiments of the present disclosure may be applied to a manipulator of a surgical robot for medical purpose that is industrially applicable.

The invention claimed is:
1. A robot arm structure comprising:
   a first robot arm unit and a second robot arm unit;
      wherein the first robot arm unit comprises:
         a plurality of first link arms,
         a first joint unit mounted on a first link arm of the plurality of first link arms and configured to rotate the first link arm about a first axis, and
         a second joint unit installed on at any of the plurality of first link arms to adjust a length of the first link arm, and
      wherein the second robot arm unit comprises:
         a second link arm,
         a third joint unit configured to rotate the second link arm about a first rotation axis to cause the second link arm to roll, the first rotation axis being different from the first axis and extending in a longitudinal direction of the second link arm, and
         a fourth joint unit arranged on an end portion of the second link arm and configured to rotate about a second rotation axis that is perpendicular to the first rotation axis;
   an instrument installed at the end portion of the second link arm and configured to be rotated by the fourth joint unit;
   the third joint unit configured to drive a yaw movement of the instrument while maintaining a preset remote center of motion (RCM) point of the instrument at a fixed location; and
   the fourth joint unit configured to drive a pitch movement of the instrument while maintaining the preset RCM point at the fixed location.
2. The robot arm structure of claim 1, wherein an imaginary extension line of the first rotation axis and an imaginary extension line of the second rotation axis do not pass through the RCM point.

3. The robot arm structure of claim 1, wherein the second link arm is connected to the first link arm so that the first rotation axis has an inclination angle with respect to the first axis.

4. The robot arm structure of claim 3, wherein the inclination angle is greater than 0° and less than 90°.

5. The robot arm structure of claim 1, wherein an end of the first robot arm unit is fixed on a location in a three-dimensional space and an opposite end of the first robot arm unit is connected to the second link arm.

6. The robot arm structure of claim 1, wherein at least one of the first joint unit to the fourth joint unit is configured to provide the robot arm structure with redundant degrees of freedom to replace a movement of another joint unit.

7. The robot arm structure of claim 6, wherein the redundant degrees of freedom allow the plurality of first link arms or the second link arm to move without changing a location and a direction of the instrument installed at the end portion of the second link arm.

8. The robot arm structure of claim 1, wherein one of the plurality of first link arms has a first portion extending in a direction parallel to a ground and a second portion bent from the first portion to be in parallel with the first axis.

9. The robot arm structure of claim 1, wherein the second joint unit comprises:
a first linear motion joint configured to linearly move along a second axis that is perpendicular to the first axis to move the second link arm; and
a second linear motion joint configured to linearly move along the first axis to move the second link arm.

10. The robot arm structure of claim 9, wherein the first link arm comprises:
a first link on which the first linear motion joint is installed; and
a second link connected to the first link, having a portion bent along the second axis, and having the second linear motion joint installed on the portion, and
wherein the first joint unit is installed on each of opposite ends of the first link or installed between the first link and the second link.

11. The robot arm structure of claim 9, wherein one of the plurality of first link arms comprises:
a first portion on which the first linear motion joint is installed; and
a second portion connected to the first portion and bent along the second axis so that the second linear motion joint is installed.

12. A manipulator of a surgical robot comprising:
the robot arm structure of claim 1; and
a passive arm structure connected to the robot arm structure and fixed when the robot arm structure is driven,
wherein the passive arm structure comprises:
a first arm extending along the first axis;
a third linear motion joint installed in the first arm and configured to move along the first axis to adjust a length of the first arm;
a fourth rotating joint installed at an end portion of the first arm and configured to rotate about the first axis;
a second arm having an end connected to the fourth rotating joint;
a fifth rotating joint installed at an opposite end of the second arm and configured to rotate about the first axis; and
a third arm having an end connected to the fifth rotating joint.

13. The manipulator of claim 12, wherein the passive arm structure further comprises a fourth linear motion joint installed on at least one of the second arm or the third arm to adjust a length of the arm.

14. The manipulator of claim 12, further comprising:
an instrument installed at an end portion of the robot arm structure,
wherein the instrument is configured to set a location of a remote center of motion (RCM) point of the instrument by driving the passive arm structure and perform a yaw movement or a pitch movement of the instrument by driving the robot arm structure while maintaining the RCM point at a fixed position.

15. A robot arm structure comprising:
a first rotating joint configured to rotate about a first axis;
a first link having an end connected to the first rotating joint;
a first linear motion joint installed in the first link to adjust a length of the first link;
a second rotating joint installed at an opposite end of the first link and configured to rotate about the first axis;
a second link having an end connected to the second rotating joint;
a second linear motion joint installed in the second link and configured to move along the first axis;
a third link connected to an opposite end of the second link and extending to have an inclination angle with respect to the first axis;
a rolling joint installed in the third link and configured to rotate about a first rotation axis, the first rotation axis being different from the first axis and extending in a longitudinal direction of the third link; and
a third rotating joint installed on an end portion of the third link and configured to rotate about a second rotation axis that is different from the first rotation axis.

16. The robot arm structure of claim 15, further comprising:
an instrument installed at the end portion of the third link and configured to be rotated by the third rotating joint,
wherein at least five joints of the first rotating joint, the second rotating joint, the first linear motion joint, the second linear motion joint, the rolling joint, and the third rotating joint are configured to be driven to make the instrument perform a yaw movement or a pitch movement while a preset remote center of motion (RCM) point is maintained at a fixed position.

17. The robot arm structure of claim 15, wherein at least one of the first rotating joint, the second rotating joint, the first linear motion joint, the second linear motion joint, the rolling joint, or the third rotating joint is configured to provide the robot arm structure with redundant degrees of freedom to replace a movement of another joint.

18. The robot arm structure of claim 17, wherein the redundant degrees of freedom allow at least one of the first link, the second link, or the third link to move without changing a location and a direction of an instrument installed at the end portion of the third link.

* * * * *